(12) United States Patent
Hara (10) Patent No.: US 10,853,622 B2
(45) Date of Patent: Dec. 1, 2020

(54) DRIVER MONITORING DEVICE (71) Applicant: TOYOTA JIDOSHA KABUSHIKI KAISHA, Toyota (JP)

(72) Inventor: Kenichiroh Hara, Yokohama (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/430,528

(22) Filed: Jun. 4, 2019

(65) Prior Publication Data

US 2019/0377933 A1  Dec. 12, 2019

(30) Foreign Application Priority Data

Jun. 8, 2018 (JP) ................. 2018-110478

(51) Int. Cl.
*A61B 5/18* (2006.01)
*G06K 9/00* (2006.01)
*A61B 5/00* (2006.01)
*H04N 5/225* (2006.01)

(52) U.S. Cl.
CPC ........ *G06K 9/00248* (2013.01); *A61B 5/0077* (2013.01); *A61B 5/18* (2013.01); *A61B 5/6893* (2013.01); *G06K 9/00281* (2013.01); *H04N 5/2253* (2013.01)

(58) Field of Classification Search
None
See application file for complete search history.

(56) References Cited

U.S. PATENT DOCUMENTS

2018/0239975 A1* 8/2018 Tamrakar .......... G06K 9/00261
2019/0056732 A1* 2/2019 Aoi ....................... G05D 1/0061
2020/0005060 A1* 1/2020 Martin ................. G05D 1/0061

FOREIGN PATENT DOCUMENTS

JP  2008-217693 A  9/2008

* cited by examiner

*Primary Examiner* — Christopher G Findley
(74) *Attorney, Agent, or Firm* — Sughrue Mion, PLLC (57) ABSTRACT

A driver monitoring device 1 comprises an imaging device 2 capturing an image of a face of a driver of a vehicle to generate an image, a face detecting part 31 detecting the face from the image, a face orientation estimating part 32 estimating a face orientation of the driver, and a cause judging part 33 judging a cause for the face not being detected. The face detecting part detects the face by extracting feature points of the face from the image. When the detection state of the face changes from "detected" to "not detected", the cause judging part judges that the cause is an eating or drinking action of the driver if in a predetermined number of images until the detection state changes from "detected" to "not detected", the face orientation is a front and the feature points at a lower region of the face are not extracted.

4 Claims, 8 Drawing Sheets

DRIVER MONITORING DEVICE

FIELD

The present invention relates to a driver monitoring device.

BACKGROUND

Known in the past has been a device for monitoring a driver of a vehicle using an imaging device provided in the vehicle to detect an abnormal action of the driver (sleeping at the wheel, distracted driving, leaving the seat, etc.) (for example, PTL 1). In this device, the face of the driver is detected from an image of the driver generated by the imaging device and the face orientation of the driver etc., are estimated based on the detected face.

However, if the driver is engaged in an abnormal action, for example, if the driver is looking at a smart phone etc., if the driver has left his seat, etc., the face of the driver cannot be detected. In this case, a warning is issued to the driver to correct the state of the driver.

CITATION LIST

Patent Literature

[PTL 1] Japanese Unexamined Patent Publication No. 2008-217693

SUMMARY

Technical Problem

In this regard, a driver sometimes eats and drinks when driving a vehicle. If the driver is eating or drinking, sometimes the face of the driver is hidden by the food or drink and therefore the face of the driver is not detected. However, if it is judged that a driver is engaged in an abnormal action due to eating or drinking of the driver and a warning is issued to the driver, the driver is liable to be bothered.

In consideration of the above technical problem, an object of the present invention is to use an imaging device to detect an eating or drinking action of a driver.

Solution to Problem

The summary of the present disclosure is as follows.

(1) A driver monitoring device comprising an imaging device capturing an image of a face of a driver of a vehicle to generate an image, a face detecting part configured to detect the face from the image, a face orientation estimating part configured to estimate a face orientation of the driver based on the image if the face is detected by the face detecting part, and a cause judging part configured to judge a cause for the face not being detected if the face is not detected by the face detecting part, wherein the face detecting part is configured to detect the face by extracting feature points of the face from the image, and when the detection state of the face changes from "detected" to "not detected", the cause judging part is configured to judge that the cause is an eating or drinking action of the driver if in a predetermined number of images until the detection state changes from "detected" to "not detected", the face orientation estimated by the face orientation estimating part is a front and the feature points at a lower region of the face are not extracted by the face detecting part.

(2) The driver monitoring device described in above (1), further comprising a warning part configured to issue a warning to the driver, wherein the warning part is configured to suppress a warning to the driver if it is judged that the cause is an eating or drinking action of the driver compared to if it is judged that the cause is something other than an eating or drinking action of the driver.

(3) The driver monitoring device described in above (2), wherein the warning part is configured to issue a warning to the driver if a state in which the state of detection of the face is not detected continues for a threshold time, and the warning part is configured to extend the threshold time if it is judged that the cause is an eating or drinking action of the driver compared to if it is judged that the cause is something other than an eating or drinking action of the driver.

Advantageous Effects of Invention

According to the present invention, it is possible to use an imaging device to detect an eating or drinking action of a driver.

DESCRIPTION OF EMBODIMENTS

Below, embodiments of the present invention will be explained in detail with reference to the drawings. Note that, in the following explanation, similar components are assigned the same reference notations.

First Embodiment

Below, a first embodiment of the present invention will be explained with reference to FIG. 1 to FIG. 7.

<Configuration of Driver Monitoring Device>

Figure 1:
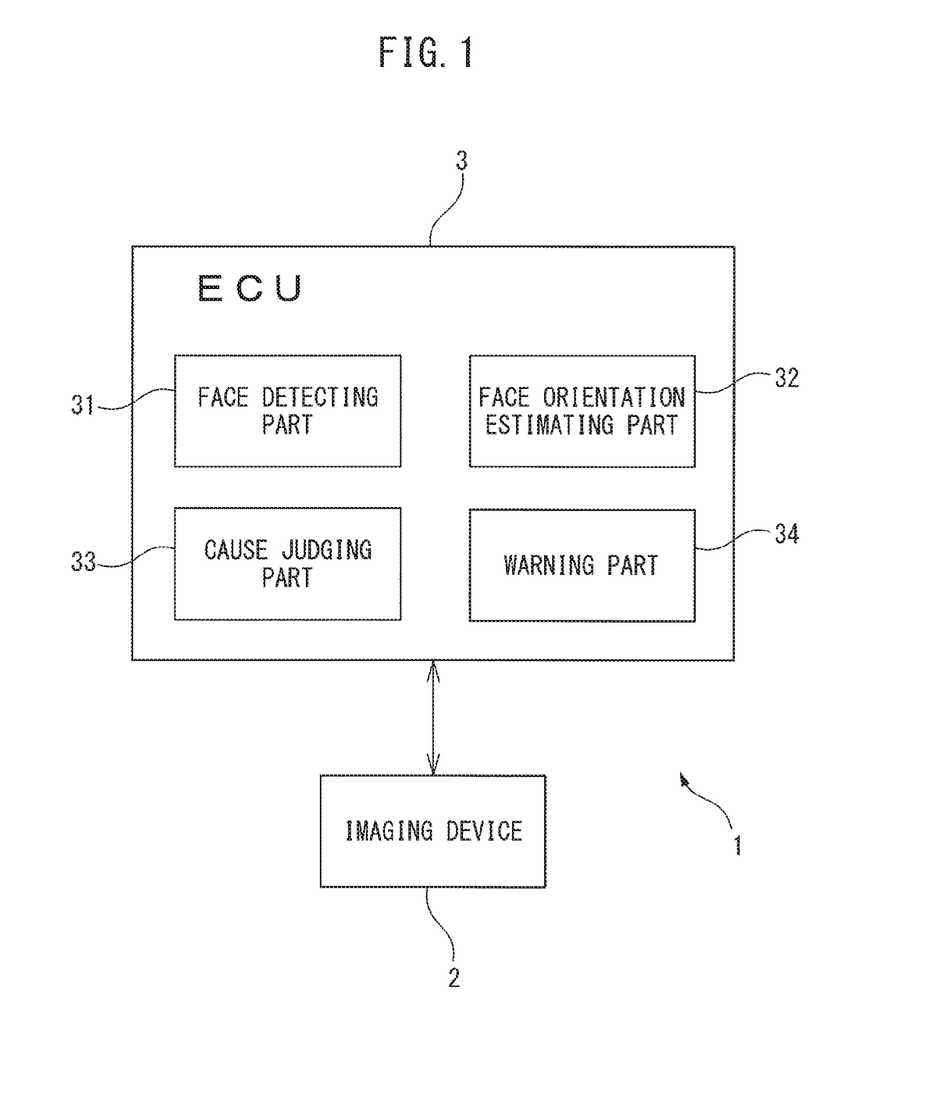
FIG. 1 is a block diagram showing the configuration of a driver monitoring device according to a first embodiment of the present invention.

FIG. 1 is a block diagram showing the configuration of a driver monitoring device according to the first embodiment of the present invention. The driver monitoring device 1 is provided with an imaging device 2 and ECU (electronic control unit) 3 and monitors a driver of a vehicle.

Figure 2:
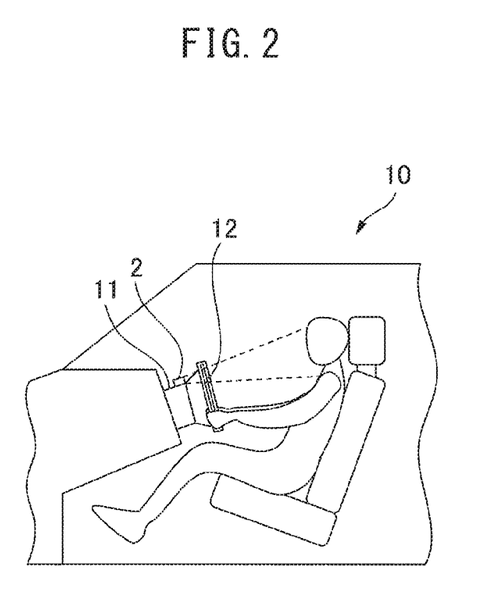
FIG. 2 is a view schematically showing the inside of a vehicle mounting a driver monitoring device.

FIG. 2 is a view schematically showing the inside of a vehicle mounting the driver monitoring device 1. The vehicle 10 is, for example, an automated driving vehicle enabling automated driving. The imaging device 2 captures the face of the driver of the vehicle 10 and generates an image. The imaging device 2 is a so-called "driver monitor camera".

The imaging device 2 is provided at the inside of the vehicle 10. Specifically, as shown in FIG. 2, the imaging device 2 is provided at the top part of the steering column 11 of the vehicle 10. FIG. 2 shows the range of capture of the imaging device 2 by broken lines. Note that, the imaging device 2 may be provided at the steering wheel 12, room mirror, meter panel, meter hood, etc., of the vehicle 10.

The imaging device 2 is provided with a camera and projector. The camera includes a lens and imaging element. For example, it is a CMOS (complementary metal oxide semiconductor) camera or CCD (charge coupled device) camera. The projector is comprised of LEDs (light emitting diodes). For example, it is comprised of two near infrared LEDs arranged at the two sides of the camera. By irradiating the driver by near infrared light, it is possible to capture an image of a face of the driver at night or another time of low light without giving an unpleasant feeling to the driver. Further, a bandpass filter for removing light of wavelength components other than near infrared is provided inside the camera and a visible light cut filter removing light of a red wavelength component from the near infrared LEDs is provided at the front surface of the projector.

The operation of the imaging device 2 is controlled by the ECU 3. For example, the imaging device 2 repeatedly captures the face of the driver at predetermined intervals when the ignition switch of the vehicle 10 is ON. The image generated by the imaging device 2 (below, simply referred to as the "image") is sent from the imaging device 2 to the ECU 3.

<Control of Driver Monitoring Device>

The ECU 3 is a microcomputer provided at the vehicle 10 and performs various control routines. The ECU 3 is provided with a memory such as a ROM (read only memory) and RAM (random access memory), a CPU (central processing unit), a power circuit, input port, output port, communication module, etc. In the present embodiment, the CPU runs computer programs stored in the memory whereby the ECU 3 functions as a face detecting part 31, a face orientation estimating part 32, a cause judging part 33, and a warning part 34. Note that, in the present embodiment, a single ECU 3 is provided, but a plurality of ECUs may be provided for the different functions.

The face detecting part 31 receives the image from the imaging device 2 and detects the face of the driver from the image. Basically, if the state of the driver is normal, that is, if the driver is fulfilling his duty of monitoring the surroundings of the vehicle 10 when driving, the face of the driver will enter the angle of view of the camera of the imaging device 2 and the face of the driver will be detected. On the other hand, if the driver is engaging in an abnormal action, for example, if the driver is blocking the lens of the imaging device 2 by his body or something he holds, if the driver is looking at his smart phone etc., if the driver leaves his seat, etc., the face of the driver cannot be detected.

The face detecting part 31 detects the face of the driver by extracting feature points of the face of the driver from the image. For example, the face detecting part 31 detects the face of the driver when the number of feature points which can be extracted is equal to or more than a predetermined value and does not detect the face of the driver when the number of feature points which can be extracted is less than the predetermined value. Further, the face detecting part 31 may detect face parts from the feature points of the face and detect the face of the driver when predetermined face parts (for example eyes and nose) can be detected and not detect the face of the driver when predetermined face parts cannot be detected.

The face orientation estimating part 32 estimates the face orientation of the driver based on the image when the face of the driver is detected by the face detecting part 31. The face orientation estimating part 32 calculates the angle of the face of the driver from the image and id the angle of the face of the driver is equal to or less than a predetermined value, estimates that the face orientation of the driver is the front. The face orientation estimating part 32, for example, estimates that the face orientation of the driver is the front if a yaw angle and a pitch angle of the face are within ±10 to ±30 degrees. The yaw angle of the face is the angle in the direction in which the driver turns his face left and right, while the pitch angle of the face is the angle in the direction in which the driver turns his head up and down.

The face orientation estimating part 32, for example, calculates the angle of the face of the driver from the image in the following way. The face orientation estimating part 32 matches face shape data when the angle of the face of the driver is 0 degree and the face region of the image. The face shape data may be data of the faces of general people or may be acquired for each driver. The face shape data is stored in the memory of the ECU 3. The face orientation estimating part 32 rotates the face region of the image so that the match between the face shape data and the face region of the image becomes maximum and calculates the angle of rotation when the match becomes maximum as the angle of the face of the driver.

Note that, the face orientation estimating part 32 may estimate the face orientation of the driver by another known method. For example, the face orientation estimating part 32 may learn large numbers of face images of drivers facing the front and estimate the face orientation of the driver by deep learning or another technique.

Figure 3:
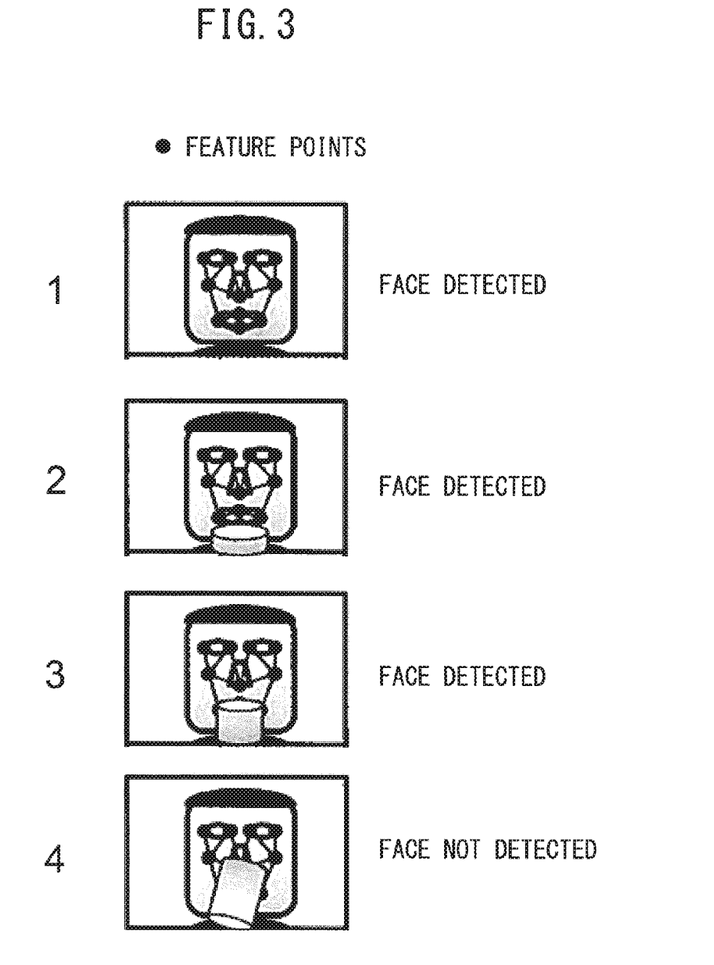
FIG. 3 is a view showing images when a driver is eating or drinking in time series.

The cause judging part 33 judges the cause for the face not being detected if the face of the driver is not detected by the face detecting part 31. FIG. 3 is a view showing images when a driver is eating or drinking in a time series. FIG. 3 shows four images. The images are generated in the order of the numbers of the images. The black dots shown in the images show feature points of the face. Note that, these feature points are an illustration. The positions and numbers of the feature points may be different from the positions and numbers shown in FIG. 3.

As will be understood from the fourth image of FIG. 3, if the driver brings food or drink (in this example, canned juice) near to the front of his face, the majority of the face of the driver will be hidden by the food or drink. As a result, in the fourth image, the face of the driver is not detected by the face detecting part 31. Therefore, as the cause for the face of the driver not being detected, an eating or drinking action of the driver may be considered in addition to the driver engaging in some abnormal action.

If the driver is eating or drinking while driving the vehicle 10, the driver tends to face the front. Therefore, if the face of the driver is detected when the driver tries to eat or drink something, the possibility is higher that the driver is facing the front. Further, usually, a driver raises food or drink from the bottom to the top. For this reason, when the driver is eating or drinking something, the feature points at the lower region of the face first become unable to be extracted among all of the feature points of the face.

Therefore, in the present embodiment, when the detection state of the face of the driver changes from "detected" to "not detected", the cause judging part 33 judges that the cause for the face not being detected is an eating or drinking action of the driver if in the past images, the face orientation estimated by the face orientation estimating part 32 is the front, and the feature points at the lower region of the face are not extracted by the face detecting part 31. The past images are a predetermined number of images until the detection state of the face of the driver changes from "detected" to "not detected". Further, the lower region of the face is the region of the bottom half part in the face region of the image and is for example the region of the mouth. According to the above control, the imaging device 2 can be used to detect the eating or drinking action of the driver.

The warning part 34 issues a warning to the driver through an HMI (human machine interface) etc., provided at the vehicle 10. Further, the warning part 34 suppresses a warning to the driver if it is judged that the cause for the face of the driver not being detected is an eating or drinking action of the driver compared to if it is judged that the cause is something other than an eating or drinking action of the driver. By doing this, it is possible to reduce the driver's discomfort due to a warning being given when eating or drinking.

For example, the warning part 34 does not issue a warning to the driver if it is judged that the cause for the face of the driver not being detected is an eating or drinking action of the driver and issues a warning to the driver if it is judged that the cause is something other than an eating or drinking action of the driver. Further, the warning part 34 may lower the strength of the warning (for example, the volume, size of the text, etc.) if it is judged that the cause for the face of the driver not being detected is an eating or drinking action of the driver compared to if it is judged that the cause is something other than an eating or drinking action of the driver.

<Processing for Detecting Face>

Figure 4:
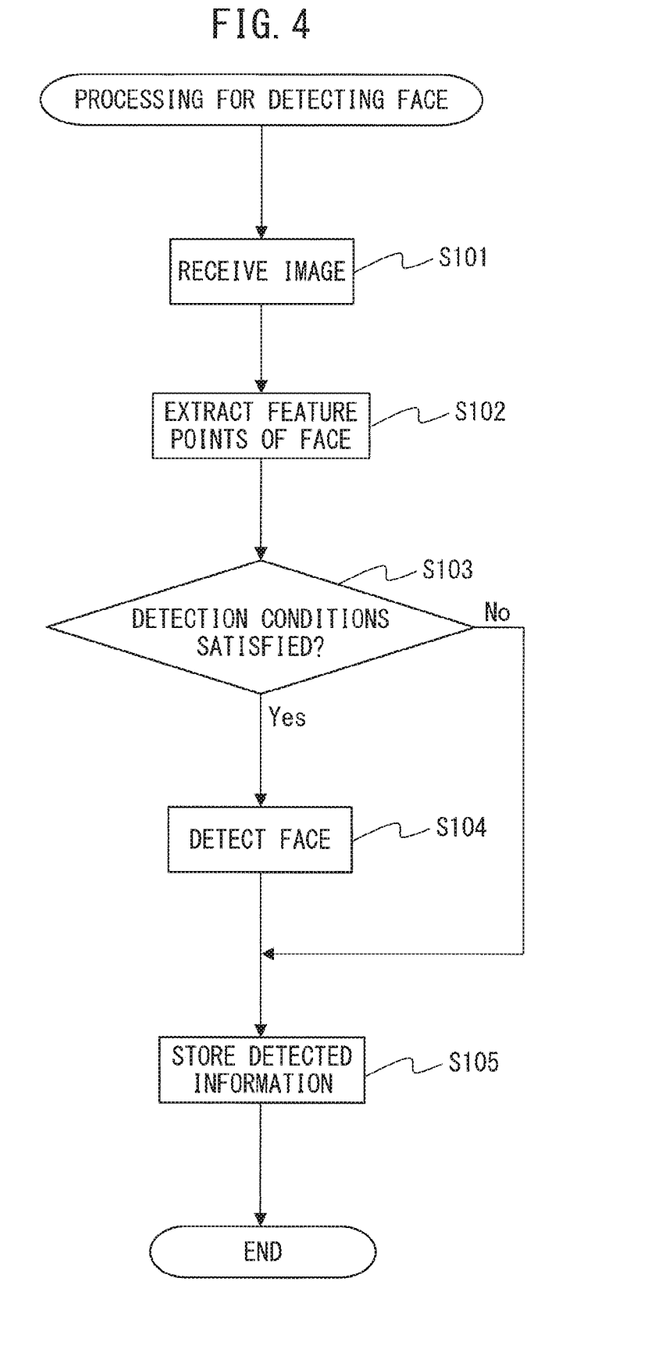
FIG. 4 is a flow chart showing a control routine in processing for detection of a face in the first embodiment.

Below, the control of the driver monitoring device 1 will be explained in detail with reference to the flow charts of FIG. 4 to FIG. 7. FIG. 4 is a flow chart showing a control routine of processing for detecting a face in the first embodiment. The present control routine is repeatedly performed at predetermined intervals by the ECU 3. The predetermined intervals are, for example, the intervals at which images are sent from the imaging device 2 to the ECU 3.

First, at step S101, the face detecting part 31 receives an image from the imaging device 2. Next, at step S102, the face detecting part 31 extracts feature points of the face of the driver from the image.

Next, at step S103, the face detecting part 31 judges whether the detection conditions are satisfied. For example, the face detecting part 31 judges that the detection conditions are satisfied if the number of feature points extracted at step S103 is equal to or more than a predetermined value and judges that the detection conditions are not satisfied if not. Further, the face detecting part 31 detects the face parts from the feature points extracted at step S103 and judges that detection conditions are satisfied if the predetermined face parts (for example, eyes and nose) can be detected and judges that the detection conditions are not satisfied otherwise.

If at step S103 it is judged that the detection conditions are satisfied, the control routine proceeds to step S104. In this case, the face of the driver can be detected, so at step S104, the face detecting part 31 detects the face of the driver. That is, detection state of the face becomes "detected".

On the other hand, if at step S103 it is judged that the detection conditions are not satisfied, the control routine skips step S103 and proceeds to step S105. In this case, the face of the driver cannot be detected, so the face detecting part 31 does not detect the face of the driver. That is, the detection state of the face becomes "not detected".

At step S105, the face detecting part 31 stores the detection information of the face in the memory of the ECU 3. Specifically, regarding the image received at step S101, the face detecting part 31 stores the detection state of the face and the positions of the not extracted feature points of the face in the memory of the ECU 3. In the memory of the ECU 3, the stored information is deleted from the oldest image so that the total number of images corresponding to these information becomes equal to or less than a predetermined number.

<Processing for Estimating Face Orientation>

Figure 5:
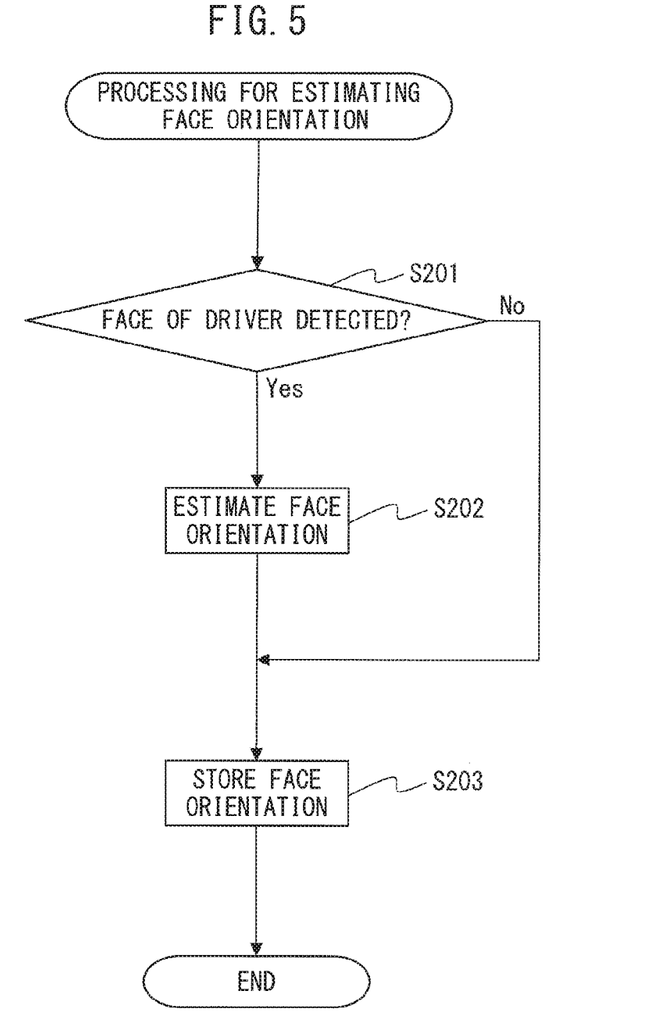
FIG. 5 is a flow chart showing a control routine in processing for estimation of a face orientation in the first embodiment.

FIG. 5 is a flow chart showing a control routine of processing for estimating a face orientation in the first embodiment. The present control routine is repeatedly performed at predetermined intervals by the ECU 3. The predetermined intervals are, for example, the intervals at which images are sent from the imaging device 2 to the ECU 3.

First, at step S201, the face orientation estimating part 32 judges whether the face of the driver has been detected by the face detecting part 31. If it is judged that the face of the driver has been detected, the control routine proceeds to step S202. At step S202, the face orientation estimating part 32 estimates the face orientation of the driver by any of the above methods.

On the other hand, if it is judged at step S201 that the face of a driver has not been detected, the control routine skips step S202 and proceeds to step S203. At step S203, the face orientation estimating part 32 stores the face orientation estimated at step S202 in the memory of the ECU 3. In the memory of the ECU 3, the stored information is deleted from the oldest image so that the total number of images for which face orientation is stored becomes equal to or less than a predetermined number. Note that, if the face orientation of the driver was not estimated (if step S202 was skipped), a predetermined face orientation other than the front is stored as the face orientation of the driver in the memory of the ECU 3.

<Processing for Judging Cause>

Figure 6:
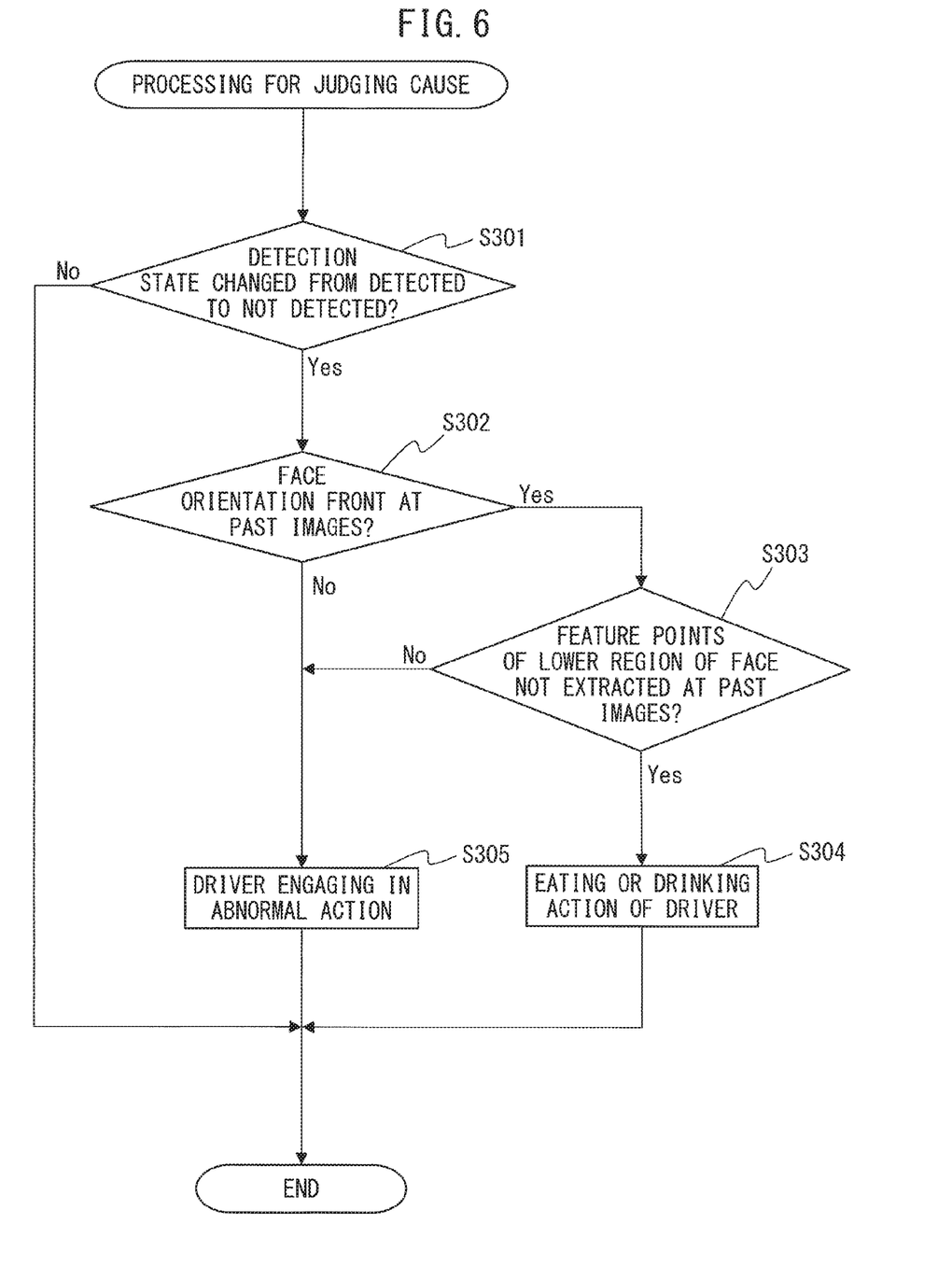
FIG. 6 is a flow chart showing a control routine in processing for judgment of a cause in the first embodiment.

FIG. 6 is a flow chart showing a control routine of processing for judging a cause in the first embodiment. The control routine is repeatedly executed by the ECU 3 at predetermined intervals. The predetermined interval is, for example, the interval at which an image is sent from the imaging device 2 to the ECU 3.

First, at step S301, the cause judging part 33 judges whether the detection state of the face has changed from "detected" to "not detected" based on the detection information stored in the memory of the ECU 3. If it is judged that the detection state of the face has not changed from "detected" to "not detected", the present control routine ends. On the other hand, if it is judged that the detection state of the face has changed from "detected" to "not detected", the control routine proceeds to step S302.

At step S302, the cause judging part 33 judges whether the face orientation of the driver estimated by the face orientation estimating part 32 is the front in the past images based on the information of the face orientation stored in the memory of the ECU 3. The past images are a predetermined number of images until the detection state of the face of the driver changes from "detected" to "not detected". Note that, the predetermined number may be 1. That is, the past images may be the one image right before when the detection state of the face of the driver changed to "not detected."

If at step S302 it is judged that the face orientation of the driver in the past images was the front, the control routine proceeds to step S303. At step S303, the cause judging part 33 judges whether feature points at the lower region of face have not been extracted by the face detecting part 31 in the past images based on the detection information stored in the memory of the ECU 3.

If at step S303 it is judged that the feature points at the lower region of the face were not extracted in the past images, the control routine proceeds to step S304. At step S304, the cause judging part 33 judges that the cause of the face of the driver not being detected is an eating or drinking action of the driver. After step S304, the control routine is ended.

On the other hand, if at step S302 it is judged that the face orientation was something other than the front in the past images or if at step S303 it is judged that the feature points at the lower region of face were extracted in past images, the control routine proceeds to step S305. At step S305, the cause judging part 33 judges that the cause for the face of the driver not being detected is the driver is engaging in an abnormal action. After step S305, the control routine is ended.

<Processing for Warning>

Figure 7:
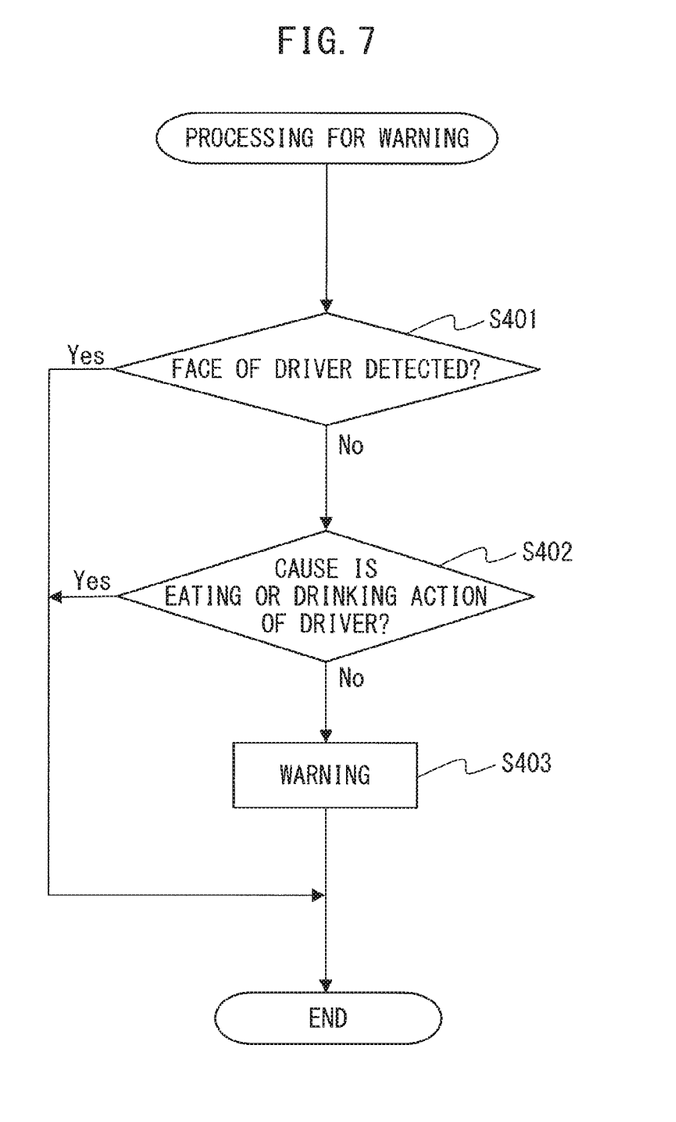
FIG. 7 is a flow chart showing a control routine in processing for issuing a warning in the first embodiment.

FIG. 7 is a flow chart showing a control routine of processing for warning in the first embodiment. The control routine is repeatedly executed by the ECU 3 at predetermined intervals. The predetermined interval is, for example, the interval at which an image is sent from the imaging device 2 to the ECU 3.

First, at step S401, the warning part 34 judges whether the face of the driver has been detected by the face detecting part 31. If it is judged that the face of the driver was not detected, the control routine proceeds to step S402.

At step S402, the warning part 34 judges whether the cause judged by the cause judging part 33 is an eating or drinking action of the driver. If it is judged that the cause judged by the cause judging part 33 is something other than an eating or drinking action of the driver, the control routine proceeds to step S403. At step S403, the warning part 34 issues a warning to the driver through the HMI etc. After step S403, the present control routine ends.

On the other hand, if at step S401 it is judged that the face of the driver was detected or if at step S402 it is judged that the cause judged by the cause judging part 33 is an eating or drinking action of the driver, the present control routine is ended without a warning being issued to the driver.

Note that, the warning part 34 may lower the strength of the warning (for example, volume, size of text, etc.) if at step S402 it is judged that the cause judged by the cause judging part 33 is an eating or drinking action of the driver compared to if at step S402 it is judged that the cause judged by the cause judging part 33 is something other than an eating or drinking action of the driver.

Second Embodiment

The configuration and control of the driver monitoring device according to the second embodiment are basically the same as the configuration and control of the driver monitoring device according to the first embodiment except for the points explained below. For this reason, below, the second embodiment of the present invention will be explained focusing on parts different from the first embodiment.

If the eating or drinking action of the driver continues for a long time, the attention of the driver is liable to wane and in turn the safety of driving of the vehicle 10 is liable to fall. For this reason, if the eating or drinking action of the driver continues for a long time, it is desirable to prompt the driver to stop eating or drinking.

In the second embodiment, the warning part 34 issues a warning to the driver if the state where the detection state of the face of the driver is "not detected" continues for a threshold time or more. Further, the warning part 34 suppresses the warning to the driver if it is judged that the cause for the face of the driver not being detected is an eating or drinking action of the driver compared to if it is judged that the cause is something other than an eating or drinking action of the driver. Specifically, the warning part 34 extends the threshold time if it is judged that the cause for the face of the driver not being detected is an eating or drinking action of the driver compared to if it is judged that the cause is something other than an eating or drinking action of the driver. By doing this, it is possible to reduce the driver's discomfort due to a warning being issued at the time of eating or drinking while suppressing long term eating and drinking.

<Processing for Warning>

Figure 8:
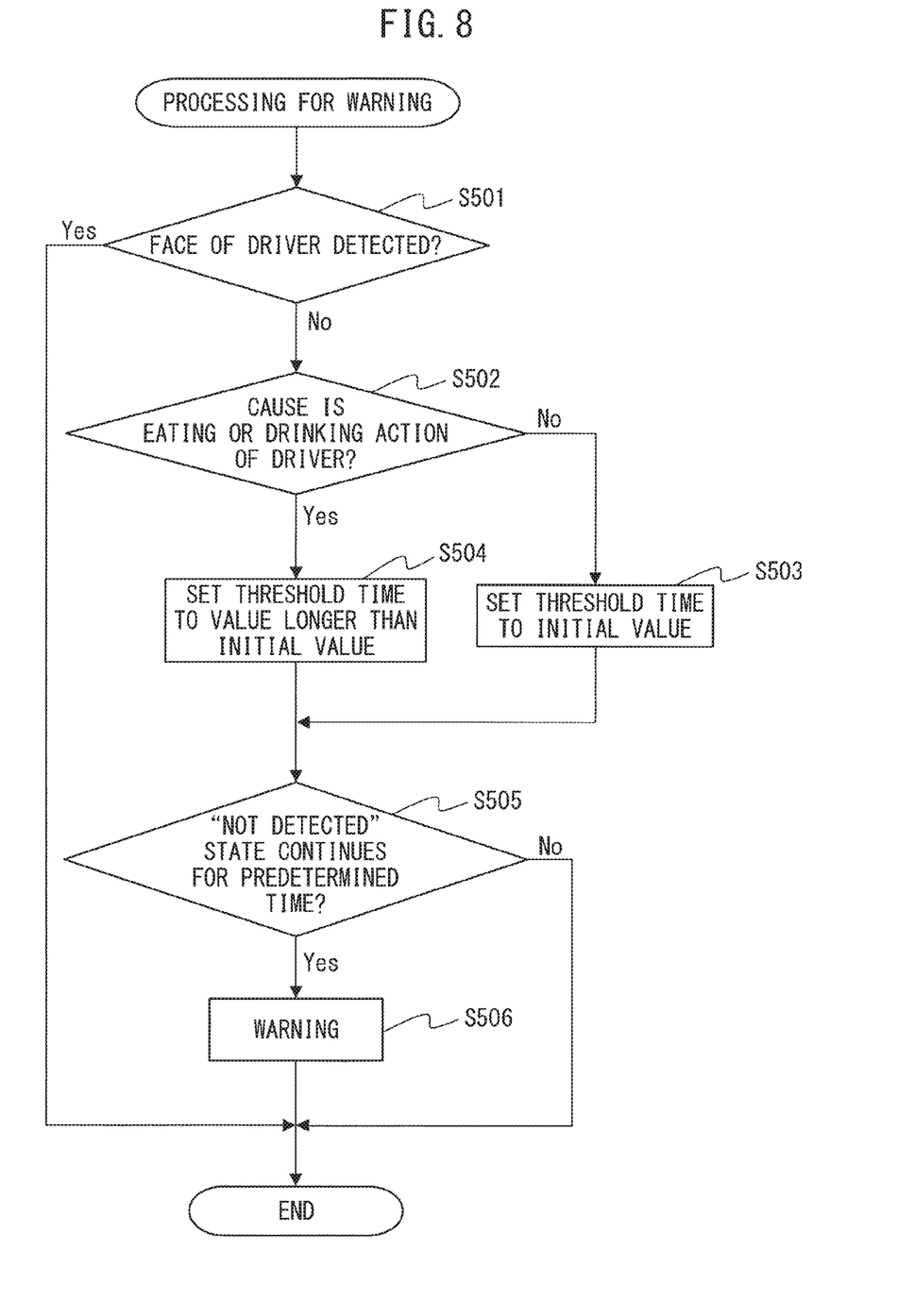
FIG. 8 is a flow chart showing a control routine in processing for issuing a warning in a second embodiment.

In the second embodiment as well, in the same way as the first embodiment, the control routines of FIG. 4 to FIG. 6 are performed. Further, in the second embodiment, instead of the control routine of FIG. 7, the control routine of FIG. 8 is performed. FIG. 8 is a flow chart showing a control routine of warning processing in the second embodiment. The control routine is repeatedly performed by the ECU 3.

First, at step S501, the warning part 34 judges whether the face of the driver has been detected by the face detecting part 31. If it is judged that the face of the driver has been detected, the control routine is ended. If it is judged that the face of the driver has not been detected, the control routine proceeds to step S502.

At step S502, the warning part 34 judges whether the cause judged by the cause judging part 33 is an eating or drinking action of the driver. If it is judged that the cause judged by the cause judging part 33 is something other than an eating or drinking action of the driver, the control routine proceeds to step S503. At step S503, the warning part 34 sets the threshold time to a predetermined initial value.

On the other hand, if at step S502 it is judged that the cause is an eating or drinking action of the driver, the control routine proceeds to step S504. At step S504, the warning part 34 sets the threshold time to a value longer than the initial value. The value longer than the initial value is determined in advance.

After step S503 or step S504, at step S505, the warning part 34 judges whether the state where the state of detection of the face of a driver is "not detected" has continued for the threshold time. If the state where the state of detection of the face of a driver is "not detected" has not continued for a threshold time, the present routine is ended.

On the other hand, if at step S505 it is judged that the state where the state of detection of the face of the driver is "not detected" has continued for a threshold time, the control routine proceeds to step S506. At step S506, the warning part 34 issues a warning to the driver through the HMI etc. After step S506, the control routine is ended.

Above, preferred embodiments according to the present invention were explained, but the present invention is not limited to these embodiments and can be corrected and changed in various ways within the language of the claims.

REFERENCE SIGNS LIST 1 driver monitoring device
2 imaging device

3 ECU
10 vehicle
31 face detecting part
32 face orientation estimating part
33 cause judging part
34 warning part

The invention claimed is:

1. A driver monitoring device comprising
an imaging device capturing an image of a face of a driver of a vehicle to generate an image,
a face detecting part configured to detect the face from the image,
a face orientation estimating part configured to estimate a face orientation of the driver based on the image if the face is detected by the face detecting part, and
a cause judging part configured to judge a cause for the face not being detected if the face is not detected by the face detecting part, wherein
the face detecting part is configured to detect the face by extracting feature points of the face from the image, and
when the detection state of the face changes from "detected" to "not detected", the cause judging part is configured to judge that the cause is an eating or drinking action of the driver if in a predetermined number of images until the detection state changes from "detected" to "not detected", the face orientation estimated by the face orientation estimating part is a front and the feature points at a lower region of the face are not extracted by the face detecting part.

2. The driver monitoring device according to claim 1, further comprising a warning part configured to issue a warning to the driver, wherein
the warning part is configured to suppress a warning to the driver if it is judged that the cause is an eating or drinking action of the driver compared to if it is judged that the cause is something other than an eating or drinking action of the driver.

3. The driver monitoring device according to claim 2, wherein
the warning part is configured to issue a warning to the driver if a state in which the state of detection of the face is not detected continues for a threshold time, and
the warning part is configured to extend the threshold time if it is judged that the cause is an eating or drinking action of the driver compared to if it is judged that the cause is something other than an eating or drinking action of the driver.

4. A driver monitoring device comprising
an imaging device capturing an image of a face of a driver of a vehicle to generate an image, and
a control device configured to detect the face from the image, estimate a face orientation of the driver based on the image if detecting the face, and judge a cause for the face not being detected if the face is not detected, wherein
the control device is configured to detect the face by extracting feature points of the face from the image, and
when the detection state of the face changes from "detected" to "not detected", the control device is configured to judge that the cause is an eating or drinking action of the driver if in a predetermined number of images until the detection state changes from "detected" to "not detected", the face orientation is a front and the feature points at a lower region of the face are not extracted.

* * * * *